United States Patent [19]

Wild

[11] Patent Number: 5,333,612
[45] Date of Patent: Aug. 2, 1994

[54] VOLUMETRIC BREAST INTEROGATION DEVICE

[76] Inventor: John J. Wild, 4262 Alabama Ave. S., Minneapolis, Minn. 55416

[21] Appl. No.: 112,148

[22] Filed: Aug. 26, 1993

[51] Int. Cl.⁵ ............................................. A61B 8/00
[52] U.S. Cl. ............................................. 128/660.9
[58] Field of Search ................. 128/660.03, 660.09, 128/660.07, 660.08, 662.03

[56] References Cited

U.S. PATENT DOCUMENTS

| | | | |
|---|---|---|---|
| 3,480,002 | 11/1969 | Flaherty et al. | 128/660.09 |
| 4,455,872 | 6/1984 | Kossoff et al. | 128/660.09 |
| 4,474,184 | 10/1984 | Harui | 128/662.03 |
| 4,483,343 | 11/1984 | Beyer et al. | 128/660.01 |
| 4,485,819 | 12/1984 | Igl | 128/660.09 |
| 4,545,385 | 10/1985 | Pirschel | 128/660.09 |
| 4,679,565 | 7/1987 | Sasaki | 128/660.01 |
| 4,722,346 | 2/1988 | Chen | 128/662.03 |
| 4,867,169 | 9/1989 | Machida et al. | 128/662.03 |
| 4,901,729 | 2/1990 | Saitoh et al. | 128/662.03 |
| 5,167,165 | 12/1992 | Brucher et al. | 128/662.03 |

*Primary Examiner*—George Manuel
*Attorney, Agent, or Firm*—James R. Cwayna

[57] ABSTRACT

A device for the rapid and complete interrogation of any portion of the body with specific attention to the breast and particularly the nipple-aerola area of the same for detection of abnormal, possibly cancerous, tissues within this normally difficult to examine area. The device includes an ultrasound transducer mounted in ultrasound conducting relationship to the area to be examined, positioned properly thereto and moved thereacross in a manner to provide a complete and systematic sweep of the area for total and rapid interrogation of the tissues within such area. The systematic sweep includes arcuate circumferential indexing of the transducer path moving radially across the breast. In this manner, the nipple-aerola area is repeatedly interrogated by each transducer travel across the breast. The transducer is also oscillated, normal to the path, as it travels along its path for cross sweep of tissue to insure total interrogation. The device may be hand held or may be suspended above the breast but maintaining transmissive contact therewith. Information gained through the interrogation is immediately revealed and detected in, "real time", instant visualization and the device includes means for physically marking the location of the abnormal tissue on the breast, with visually discernable indicia, making maximally efficient mass screening of the populus possible.

6 Claims, 2 Drawing Sheets

VOLUMETRIC BREAST INTEROGATION DEVICE

RELATED APPLICATIONS

There are no applications by applicant currently on file in the United States Patent Office by applicant which relate in any manner to this application nor which would effect the prosecution of this application.

FEDERAL SPONSORSHIP

This invention is not made under any Federally sponsored research and development arrangement nor any other sponsored research and development arrangement which should be noted.

FIELD OF THE INVENTION

This invention relates generally to devices for interrogation of tissues of the human body to determine the presence of abnormal tissues and more specifically to an ultrasonic interrogation device for rapid; complete and systematic interrogation of the tissues of both male and female breasts, particularly the nipple-aerola area of the female breast, which is one of the common sites of tumors, for the instantaneous, "real time", revelation of tumors or other tissue abnormalities.

SUMMARY OF THE INVENTION

A device for the rapid, systemmatic and complete interrogation of the various tissues of the human body and particularly, the female breast and more particularly the nipple-aerola area thereof through the use of ultrasound and related electro-acoustic techniques.

The physical portions of the device include a fluid fillable, ultrasound conductive housing having an ultrasound transducer mounted therein with mechanical transport devices to move the transducer within the housing for total coverage of the breast volume with repeated covering of the nipple-aerola area of the breast with the transmitted and echoed ultrasound beam to ensure complete interrogation thereof with multiple "lines of acoustic sight".

The housing is positionable over the breast through hand manipulation or mechanical means and the transducer is moved in a diametric, straight line path across the housing, hence the breast, while the transducer is oscillated in a direction normal to the straight line diametric movement. Following completion of a movement along one such straight line path, the device is circumferentially indexed to provide multiple arcuate indexing and thus total and repeated interrogation of the breast volume. In this manner, indexing through 180°, provides for full breast coverage and multiple, repetitive coverage through the nipple-aerola area.

The defined paths provide for total breast volume coverage with particular interrogation emphasis being placed on the nipple-aerola area of the breast.

BACKGROUND AND OBJECTS OF THE INVENTION

Applicant is well aware of the utilization of ultrasound as a tool for the detection of tissue abnormalities and is the inventor and owner of U.S. Pat. No. 3,854,767 entitled "Ultrasonic Method for Systematic Search and Detection of Tissue Abnormalities". He has, in addition to this invention and resultant patent, authored many articles concerning the use of ultrasound for the detection of tissue abnormalities.

The applicant's work in the field of ultrasound as a tissue abnormality detection tool has resulted in international recognition of his contributions as the same is set forth in the Prior Art Statement and he has been recognized as the person responsible for the introduction and utilization of pulse-echo ultrasound to diagnostic medicine.

It is considered that twenty-eight percent of breast cancers occur within the nipple-aerola area of the breast and this area is of particular import to the complete interrogation of the female breast. Applicant's device provides for the instantaneous, high black and white contrast, visual readout of occurring abnormalities with particular emphasis on such area with such readout suitable for abnormality screening in "real time" on an efficient basis. This approach to interrogation, besides being effective and efficient, eliminates cumbersome and costly record keeping.

The mechanical movements of applicant's device provide for circumferentially indexing the diametric straight line travel of the ultrasound transducer with oscillatory motion being provided to the transducer in a direction normal to the straight line path for resultant, complete tissue interrogation by the ultrasound beam to maximally detect slight tissue differences in diffuse back-scattered acoustic energy.

It is therefore an object of the applicant's invention to provide an ultrasound, tissue abnormality detection device for the rapid, systematic and complete examination of various anatomical body parts and particularly the female breast with particular attention being given to the nipple-aerola area thereof at which site maximum differerential acoustic echoing is detectable.

It is a further object of the applicant's invention to provide a tissue abnormality detection device which includes the conductive isolation of an ultrasound transducer in position and positionable and transportable across the female breast to provide a real time, instanteous, high black and white visual contrast readout of the abnormalities that may occur in the tissues of the female breast.

It is still a further object of the applicant's invention to provide an ultrasound transducer operative in interrogative relation to the female breast and to move the same through straight line, arcuately indexed and oscillatory motions providing multiple "Lines of Acoustic Site" for complete interrogation of the tissues of the breast for the determination of tissue abnormallity presence.

These and other objects and advantages of the applicant's invention will more fully appear from a consideration of the accompanying disclosure and drawings of a preferred form of the invention.

DESCRIPTION OF A PREFERRED FORM OF THE INVENTION

Figure 1:
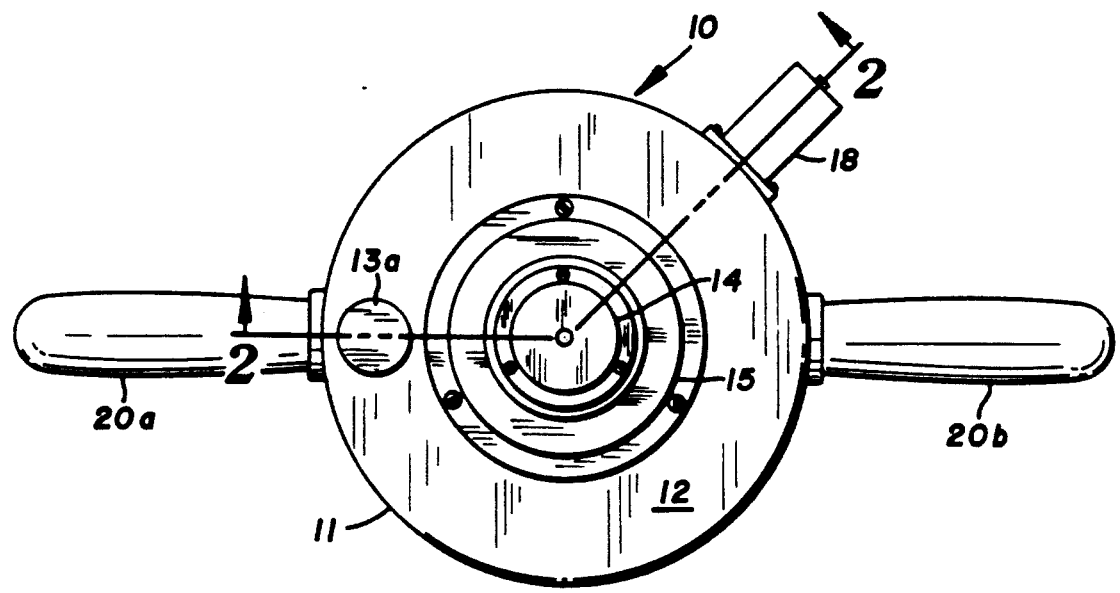
FIG. 1 is a top plan view of a hand held version of the invention embodying the concepts thereof.
Figure 2:
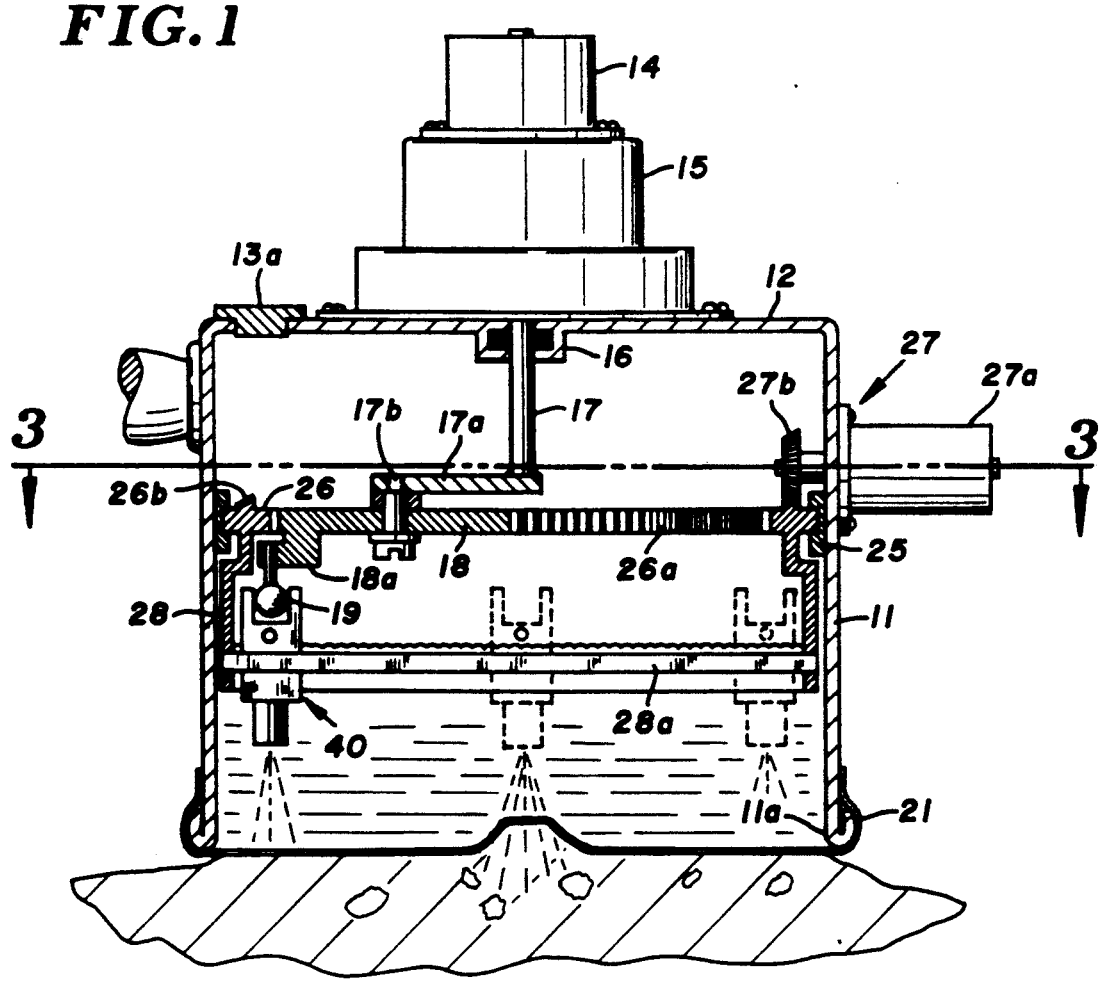
FIG. 2 is a vertical section taken substantially along Line 2—2 of FIG. 1.

In accordance with the accompanying drawings, applicant's device for the complete, rapid and systematic interrogation of the tissues of various anatomical body parts and particularly the female breast with particular attention to the nipple-aerola area thereof is generally designated 10 and is illustrated in its use position upon a breast in FIG. 2 of the drawings.

In the form shown, the unit 10 includes an inverted, U-shaped housing defined by a generally arcuate side wall 11 and an upper closure and support surface 12 having a filling hole 13 and associated cap 13a for filling the same with ultrasound conductive fluid such as water. Top 12 also provides support for mounting of a resolver 14 and drive motor 15. Top 12 also provides drive bearing mounting means 16 for rotative housing of a drive crank 17, the function of which is described hereinafter. An indexing means such as motor 27 is provided on side wall 11. Oppositely disposed handles, 20a. 20b are also provided on side wall 11.

Lower end 11a of housing side wall 11 is provided with a flexible, liquid proof seal 21 extending thereacross to contain the liquid conducting medium within the housing.

The entire drive mechanism and ultrasound transducer is contained within the housing. Obviously the transducer element is submersed within the confined liquid to insure proper ultrasound transmission to and from the tissues being interrogated and seal member 21 is formed of a material which permits transmission without signal deterioration.

Figure 3:
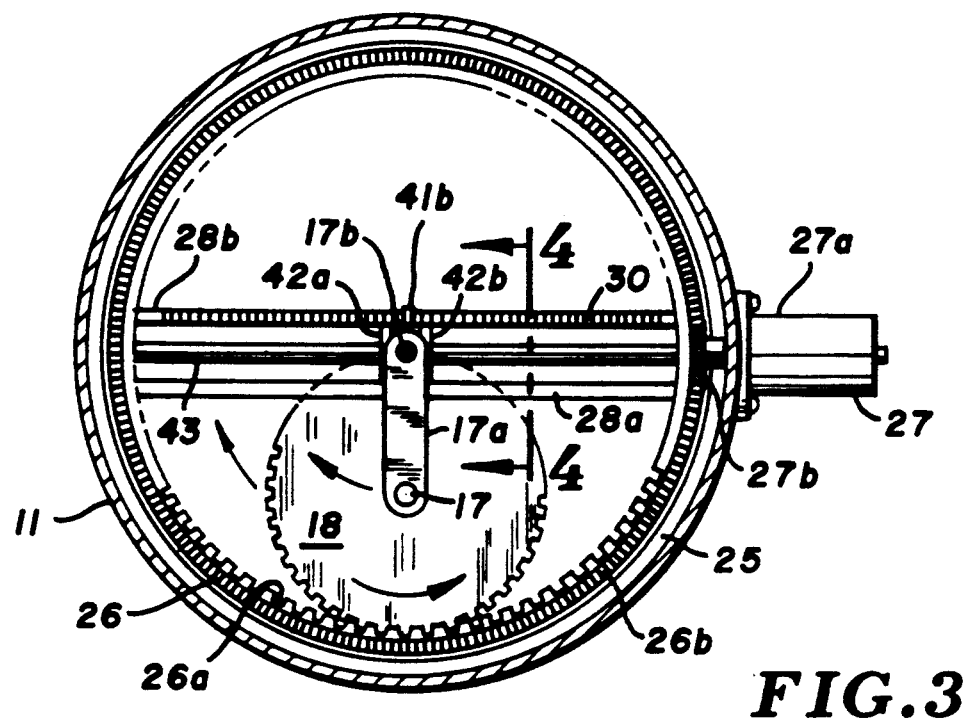
FIG. 3 is a horizontal section taken substantially along Line 3—3 of FIG. 2; and, FIG. 4 is a vertical section taken substantially along Line 4—4 of FIG. 3.
Figure 4:
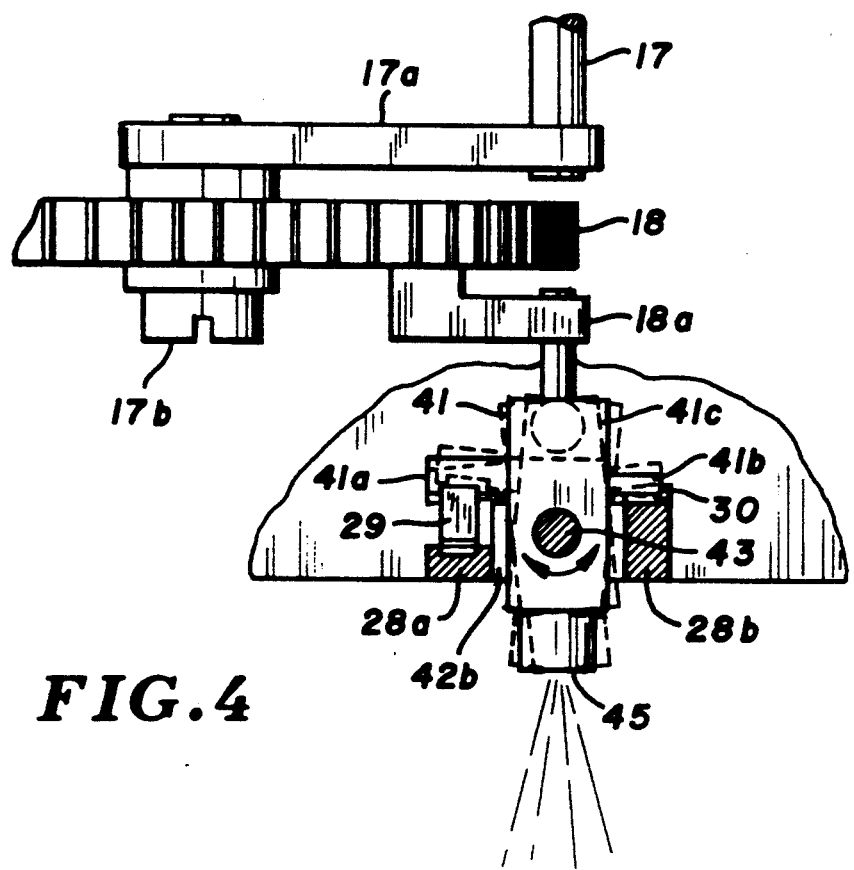

The chosen method of transducer transport through its desired paths is best illustrated in FIGS. 2, 3 and 4.

It should be obvious that the mechanical means of transport illustrated are illustrative of many devices that could be utilized to achieve the same travel and transport results without departing from the scope of the invention. Similarly, the unit could be hand manipulated across the area of interrogation by initially applying a conductive material, such as a thixotropic gel or other energy transmissive lubricant to the surface of the area to be interrogated and thereafter manually moving the unit across such area while maintaining direct surface contact. Such a manual operative arrangement would not give the positive energy transmission as the means described herein nor would it insure total interrogation with repetitive interrogation of, for example, the nipple-aerola area.

A ring gear support 25 is secured to the inner surface of housing side wall 11 and, in the form shown is H-shaped to provide an upper and lower guiding surface to ring gear 26. Ring gear 26 provides inner teeth 26a and an upper bevel gear section 26 entirely therearound. Drive unit 27 including indexing drive 27a and bevel gear 27b is mounted on side wall 11 to mesh with ring gear 26b. The function of drive unit 27 is to provide arcuate indexing to the transducer unit and with proper incremental indexing it should be obvious that thorough examination of the breast is obtainable.

A downwardly depending skirt 28 is affixed to the lower surface of ring gear 26 and a pair of transducer activating bars 28a, 28b are provided to extend diametrically across the lower end of skirt 28. The first of such bars 28a simply provides a biasing spring stop against which biasing member 29 will ride for return shifting of transducer housing 41. The second of such bars 28b is provided to initiate oscillatory movement of housing 41 by the provision of a ripple bar 30 thereon for engagement with an actuation arm provided on the housing 41.

Transducer housing 41 is, in the form shown, a cylindrical housing having means for retaining the piezoelectric crystal 45 at the lower end thereof with a pair of actuation arms 41a, 41b extending outwardly therefrom and having a ball receiving recess 41c at the upper end thereof. Transducer housing 41 is mounted for oscillation on shaft 43 which is positioned parallel to bars 28a, 28b by cross bars 42a, 42b mounted on bars 28a, 28b. Obviously movement of the transducer housing 41 along and between the path of bars 28a, 28b results in arm 41b moving over the tops of the ripples of bar 30 to move in following response thereto and will be returned by arm 41a acting against biasing spring 29. In this manner, the transducer housing 41 and thus transducer 45 is caused to oscillate along the diametric path. The oscillatory movement of housing 41 is illustrated by the dotted lines of FIG. 4.

Means for driving and crystal 45 in straight line fashion includes, as selected, a hypo-cycloidal drive utilizing the internal ring gear teeth 26a as the stationary element of such drive. As is known, a hypo-cycloidal drive is a basic gear drive for converting rotary motion to straight line motion. Rotary power is delivered from shaft 17 to positively drive crank 17a which is; in turn rotatably connected to pinion through shaft 17b. A positive crank arm 18a is arranged below pinion 18 and drive ball 19 is secured thereto. The combination of the pinion 18 acting within the ring gear produces the straight line motion of transducer housing 41 and carried crystal 45 across the housing and thus the area to be interrogated.

Applicant has described three different interrogation directions of travel or shifting of the transducer. These include the diametric, straight line path, the circumferential indexing of the diametric path and the oscillatory movement of the transducer in a direction normal to the diametric path.

These motions of travel are particularly selected such that the travel of the transducer will be congruous to the anatomical structure of the breast. Basically, the breast structure may be likened to an orange which is divided into a plurality of sectors or sections. Obviously, the circumferential indexing of the diametric path then similates the sectorial pattern of the breast and likened orange with the oscillation of the transducer increasing the acoustic sight line for complete interrogation of the breast tissues.

Obviously electro-acoustic connective devices must be provided for actuation of the mechanical devices illustrated herein and the transmission of ultrasonic energy to and from crystal 45.

In use, the unit is placed over the breast and power is supplied to the drive devices with ultrasonic energy being provided to the piezoelectric crystal. As the crystal 45 traverses the interrogation area, the user is afforded an actual, real time, black and white contrast picture of the tissue underlying the skin. Inflamed or tumorous tissue areas provide totally different; visually available echoes than those of normal tissues and the image is immediately available to the operator of the device.

It should be noted that the diametric path of transducer provides a "linear" path for beam travel and this could similarly be accomplished by providing a linear array of transducers arranged in end-to-end relation with electro-acoustic means being provided for sequential or simultaneous energization of the same with means provided for interpreting the echoed tissue information. Similarly, the individual linearly aligned beams could be oscillated from side-to-side.

The objects and advantages of applicant's device have been clearly established to be the systematic, rapid and complete interrogation of any anatomical body part including the breast and particularly the nipple-aerola area of the breast.

What is claimed is:

1. A device for the detection of tissue abnormalities through the use of pulse-echo ultrasonic energy, including:
   a. a circumferential housing providing at least an upstanding side and of a diameterto sufficiently extend over an anatomical area, such as a women's breast, for which examination and detection of such abnormalities is desired;
   b. an ultrasound transducer mounted and arranged in said housing and being shiftable therein to transmit and receive energy from the anatomical area to be interrogated as to the presence of abnormalities;
   c. means for driving said transducer across said housing in a diametric, straight line path;
   d. means for circumferentially indexing said straight line path of said transducer wherein each path in which said transducer is driven will cross the central area of said housing; and,
   e. means for delivering to and receiving ultrasonic energy to and from said transducer.

2. The device as set forth in claim 1 and said transducer including a piezoelectric crystal for transmission and receipt of ultrasonic energy.

3. The device as set forth in claim 2 and means for oscillating said transducer in a direction normal to said diametric, straight line path as the same is driven along said path.

4. The device as set forth in claim 1 and means for providing and maintaining ultrasonic energy conductivity between said ultrasound transducer and the anatomical area of interrogation.

5. The device as set forth in claim 4 and said housing including being fluid retaining providing at least a bottom and said upstanding side, said bottom being energy transmitting.

6. The device as set forth in claim 5 and said housing being at least partially fillable with an ultrasonic energy transmitting fluid, said transducer and associated crystal being submersed within such fluid.

* * * * *